United States Patent [19]

Prevo

[11] 4,359,013
[45] Nov. 16, 1982

[54] DEVICE FOR SPREADING MONOLAYERED FILMS

[76] Inventor: Donald L. Prevo, 907 Linden Ave., Winnetka, Ill. 60093

[21] Appl. No.: 185,020

[22] Filed: Sep. 8, 1980

[51] Int. Cl.³ .................. B05C 11/04; B05C 13/02; B05C 17/10
[52] U.S. Cl. .................. 118/100; 15/104 S; 118/500
[58] Field of Search ............ 118/100, 120, 500; 15/104 S; 427/2; 101/269, 354, 355; 350/92; 108/28

[56] References Cited

U.S. PATENT DOCUMENTS

| | | | |
|---|---|---|---|
| 2,655,898 | 10/1953 | McNeil | 118/506 |
| 2,746,075 | 5/1956 | Gardner | 15/104 S |
| 3,683,850 | 8/1972 | Grabhorn | 118/100 |
| 3,880,111 | 4/1975 | Levine et al. | 118/100 X |
| 3,888,206 | 6/1975 | Faulkner | 118/100 |
| 4,030,341 | 6/1977 | Sullivan | 73/61.1 C |
| 4,151,915 | 5/1979 | Levine et al. | 206/456 |

FOREIGN PATENT DOCUMENTS 830429 7/1938 France .
2315693 1/1977 France .

*Primary Examiner*—Evan K. Lawrence
*Attorney, Agent, or Firm*—McDougall, Hersh & Scott

[57] ABSTRACT

A spreader, movable over a base, for coating a microscope slide or the like mounted on a supporting surface of the base with a single uniform layer of a fluid. The spreader comprises a support having legs for engaging the supporting surface, pressure pads for engaging the slide to hold the support above the slide having a fluid thereon and a bar extending transversely along the lower surface of the support for uniformly spreading the fluid to create a monolayered film on the upper surface of the slide as the spreader is drawn over the slide. The bar has a flat section which is maintained parallel to the slide and sloped surfaces extending upwardly toward the support from the flat section. Ramps are provided in tracks of the base to permit the bar to evenly disengage from contact with the film.

14 Claims, 6 Drawing Figures

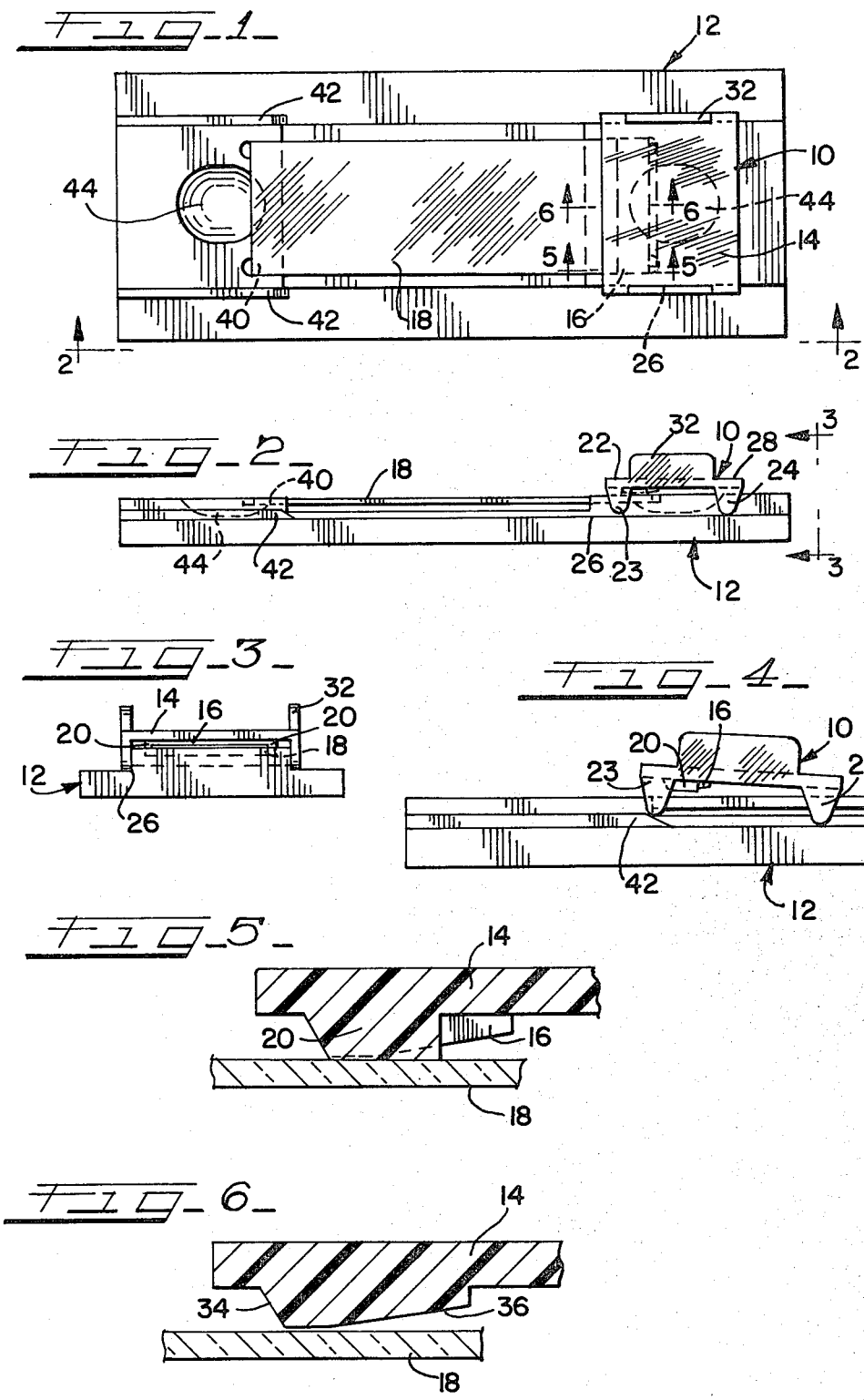

DEVICE FOR SPREADING MONOLAYERED FILMS

BACKGROUND OF THE INVENTION

The present invention relates generally to the preparation of monolayered films for use in the microscopic examination of fluids. In particular, the invention is a portable device for uniformly smearing a cellular fluid on a microscope slide or the like without substantially altering the morphology of the components in the fluid.

It is estimated that the medical profession performs between 500 and 600 million venipunctures annually. The drawn blood samples are routinely examined by microscopy so that individual cells can be observed and abnormal cells identified. The cells, when distributed in a single layer on a slide and treated with a stain, can be counted to provide an index with which to diagnose the condition of the patient.

An elementary method of preparing a slide film for microscopic examination is to place a small quantity of a fluid, such as blood, on a slide. If a thin sample layer is desired, a second slide is placed over the first so that the fluid is dispersed between the two slides by drawing the slides together. The drawing action of this manual smear technique can produce an inconsistent distribution of cells with considerable cell overlapping and render a cell count imprecise. Cells may also be mechanically stretched and deformed, thus making a proper evaluation of cell morphology difficult.

Alternatively, the second slide can be held at an angle with respect to the first slide and drawn across the upper surface of the latter. A constant angle between the slides must be maintained during the drawing motion; the angle is critical to the smearing of a uniform film, but such precision is difficult to attain. As a result, smears produced by this method are often streaked and unevenly distributed.

Rather than drawing the slides together, the slides can be centrifuged to evenly distribute the fluid. In this manner, the mechanical deformation of cells is minimized. Centrifugation, however, requires expensive equipment and once the centrifuge apparatus is positioned and balanced, it cannot be moved conveniently so the technique must be performed at a single location.

Thus, the need exists for a device for preparing a fluid sample for microscopic examination wherein a uniform distribution of cells is achieved and cell deformation is minimized. It is also advantageous to have an inexpensive, portable device. The present invention is directed to the fulfillment of these needs.

PRIOR ART STATEMENT

In accordance with the provisions of 37 CFR § 1.97, applicant advises that the following U.S. patents are the closest prior art of which he is aware:

U.S. Pat. No. 3,880,111 to Levine et al.;
U.S. Pat. No. 3,888,206 to Faulkner; and
U.S. Pat. No. 4,151,915 to Levine et al.

U.S. Pat. No. 3,880,111 to Levine et al. discloses an automatic device for preparing blood smears. A glass spreader is first pushed mechanically towards a drop of blood located at one end of a slide. After the spreader contacts the blood, a sufficient dwell time is allowed to permit the blood to diffuse along the lateral edges of the spreader. The spreader is then pulled in the reverse direction away from the blood sample at a predetermined speed. The spreader of Levine et al. thus advances to a predetermined point on the slide and then retracts to its original position; the spreader of the present invention, on the other hand, pushes the fluid across the slide. In addition, the device of the present invention is a simple, portable device that is operated manually. Levine et al. disclose a relatively complex, electrically operated device.

One major disadvantage of the invention of U.S. Pat. No. 3,880,111 to Levine et al. is the problem of motor vibration which can produce a chattering on the smear. U.S. Pat. No. 3,888,206 to Faulkner highlights this problem since Faulkner merely improves the aforementioned device of Levine et al. by adding a linkage assembly with shock absorbing means to dampen the vibrations and chatter which result during operation of the device.

U.S. Pat. No. 4,151,915 to Levine et al. discloses another mechanical device for smearing a liquid on a slide. As with the previously described devices, the spreader is advanced to a predetermined point on the slide and then is retracted to its original position. The device is manually operated, but is still complex when compared to the construction and use of the present invention.

None of these patents show, or even contemplate a simple hand-held device for smearing uniform monolayers of a fluid.

SUMMARY OF THE INVENTION

The invention is a device for depositing a uniform monolayer of a fluid on a planar surface, such as a slide, for use in the microscopic examination of the fluid. A base includes a supporting surface that holds the slide or the like on which is placed a small quantity of the fluid. A spreader comprising a support having legs removably positioned on the base and pressure pads in contact with the slide holds the support above the slide. A bar on the lower surface of the support is in close proximity with the slide so that as the spreader is drawn across the slide the bar uniformly smears the fluid by capillary action as a monolayer. The fluid can then be dried to form a film which can be stained before analysis.

It is, therefore, the principal object of this invention to provide an improved device for the preparation of monolayered films. The films are uniform and suitable for use in microscopic analyses.

A further object of this invention is to provide a novel spreader for the preparation of monolayered films which is relatively economical and which can be disposed of after use, thereby avoiding any problems of contamination of specimens.

Other objects and advantages will be apparent from the following detailed description made with reference to the accompanying drawings.

BRIEF DESCRIPTION OF THE DRAWINGS

FIG. 1 is a top view of one embodiment of the invention;

FIG. 2 is a side view taken along the line 2—2 of FIG. 1;

FIG. 3 is an end view taken along line 3—3 of FIG. 2;

FIG. 4 is a partial side view of the invention illustrating the interaction of the spreader and the ramps of the base;

FIG. 5 is a sectional view taken along the line 5—5 of FIG. 1; and

FIG. 6 is a sectional view taken along the line 6—6 of FIG. 1.

DETAILED DESCRIPTION

As illustrated in the drawings, the apparatus of the invention comprises a spreader 10 and a base, such as designated by reference numeral 12, which cooperates with the spreader. Both the spreader 10 and base 12 may be molded from a material of a kind that will flow when subjected to heat and pressure, and which is rigid when cooled, such as a thermoplastic. In addition, the base 12 can be constructed of any other durable material. The base is reuseable, while the spreader is disposable. Use of the device of the invention permits the uniform application of any fluid monolayer on a microscope slide or the like with a single motion of the spreader 10 over the base. Because a new spreader is used for each coating operation, uniform fluid samples can be deposited without contamination by previously deposited samples.

The spreader 10 in the illustrated embodiment comprises a support 14 and a bar 16 extending transversely across the bottom of the support for uniformly smearing the fluid monolayer on the upper surface of a microscope slide 18. The spreader 10 is maintained above the slide 18 by contact with the base 12 and the slide at four points. Specifically, a pressure pad 20 located at each end of the bar 16 (see FIG. 3) rests on the upper surface of the slide to hold the front end 22 of the spreader at a predetermined distance above the slide, and a set of rear legs 24 rest within tracks 26 on the base to hold the rear end 28 of the spreader in position. The front legs 23 do not rest on the base, as illustrated in FIG. 2, but simply serve to guide the front end 22 of the spreader and to prevent lateral movement of the spreader during the drawing motion. Handles 32 may be provided to facilitate gripping and drawing the spreader 10 over the slide 18.

As best shown in FIGS. 5 and 6, the bar 16 includes sloping anterior and posterior surfaces 34 and 36, respectively. A flat section 38 is located between the sloping surfaces. When the spreader 10 is positioned above the top surface of the slide 18, the anterior surface 34 of the bar 16 extends at an angle to the planar slide surface. In preferred embodiments, that angle is between 60° and 80° to the slide surface for the forming of whole blood films. The posterior surface 36 of the bar 16 defines an angle of approximately 10° with respect to the aforesaid planar slide surface. Variations within 60° to 80° in the anterior angle produces a uniform film of a blood sample that is satisfactory for microscopic analysis.

In addition, a variation in the anterior angle produces a change in the thickness of the film deposited by the spreader. For example, when blood is the fluid to be spread as a film, a change from 80° to 60° in the anterior angle produces a thicker film. The device, therefore, can be constructed to spread monolayered films of a predetermined thickness. It will be understood that fluids in addition to blood, such as urine, mucus or a bacteria culture medium can be uniformly deposited on slides by the present invention, assuming appropriate dimensional changes are made in both the spacing between the flat section 38 of the bar 16 and slide 18 and in the angles of the anterior and posterior surfaces 34 and 36 of the bar. Fluids containing particulate matter or sediment also may be deposited as monolayers.

Referring again to FIG. 1, the base 12 securely holds within a recess 40 the slide 18 which is to be coated with the fluid. Tracks 26 on the base guide the front and rear legs 23 and 24, respectively, of the spreader 10 during the drawing motion. As best illustrated in FIG. 4, a ramp 42 at the end of each track 26, when in contact with the front legs 23, lifts the spreader 10 and thus the bar 16 from the proximity of the top surface of the slide 18 at the end of the drawing motion.

In the practice of the invention, a slide 18 is placed within the recess 40 of the base 12. A drop of the fluid to be smeared is placed at one end on the top surface of the slide 18. The spreader 10 is then placed on the base 12 so that the front and rear legs 23 and 24 of the spreader ride in the tracks 26 of the base. With a single motion the spreader 10 is drawn slowly over the fluid droplet and across the slide 18. The pressure pads 20, when in contact with the slide 18, maintain a fixed distance between the bar 16 and the slide surface. The flat section 38 of the bar 16 is in close proximity with the top surface of the slide 18 during the drawing motion, and consequently the fluid is spread between the flat section 38 and the slide 18. As the bar 16 reaches the end of the slide 18, the front legs 23 of the spreader 10 engage the ramps 42 within the tracks 26 to lift the bar 16 from the slide 18 and to break evenly the contact between the slide 18, fluid and bar 16. (See FIG. 4). Alternatively, the spreader 10 may be lifted by the operator or by other means directly from the surface of the slide. Fingerholds 44 may be provided to allow the slide to be removed easily from the base 12 without deforming the film.

The advantage of a single motion in the application of the fluid lies in the decrease in shear forces to which the fluid is subjected. While a shear force does result from the movement of the spreader 10 across the slide 18, the single pass of the spreader 10 produces less distortion of sample cells than the drawing action of one slide in contact with another, between which the fluid is sought to be dispersed. The bar 16 does not contact the slide during the drawing motion, but a fixed distance between the bar and the slide is maintained. This fixed distance minimizes the possibility of shearing and deforming the cells as the spreader is moved over the slide.

The fluid is advanced along the slide 18 during the drawing motion by the capillary action resulting from the proximity of the bar 16 to the slide. Capillary action is a force that is the resultant of the adhesion, cohesion and surface tension in a liquid which is in contact with a solid, as in a capillary tube. When the cohesive force is greater, the surface of the liquid tends to rise or advance in the tube; when the adhesive force is greater, the liquid surface tends to be depressed in the tube.

When a sample of whole blood is deposited, a gap of approximately 0.010 inch between the bottom of the bar 16 and the top surface of the slide has been found to produce an even distribution of blood cells. The anterior and posterior sloping surfaces 34 and 36 of the bar 16 should be sufficiently smooth to insure an even contact between the bar 16 and the fluid. An uneven contact could produce streaking of the sample and, in the case of a whole blood sample, considerable red blood cell overlapping.

This invention represents a sharp departure from conventional methods of forming fluid smears or films. A basic feature of the apparatus is the ability to hold and to distribute a fluid between two parallel planes as the spreader 10, which defines a first upper plane, is drawn over the slide 18 forming a second, lower plane. In particular, the upper plane of the spreader comprises the flat section 38 located on the bottom of the bar. This upper plane remains equidistant and parallel to the lower plane, the surface of the slide, during the drawing motion of the spreader over the base 12.

A third plane, parallel to and below the two aforementioned planes, is defined by the tracks 26 of the base 12. The maintenance of this parallel configuration of the three planes and of a constant distance between the flat section 38 and the slide 18 is critical to the forming of unstreaked films having a uniform distribution of components. During the drawing motion, the pressure pads 20 of the spreader 10 move along the surface of the slide 18 and thus ensure parallelism between the bar 16 and the slide while the rear legs 24 of the spreader move within the tracks 26 of the base 12 to ensure parallelism between the bar and the base.

In addition, the cooperation of the anterior and posterior angles is essential to the production of the capillary action necessary for the forming of a uniform, unstreaked film. The constant anterior angle of the bar holds the fluid under a given surface area defined by the anterior sloping surface 34 and the flat section 38, while the constant posterior angle of the posterior sloping surface 36 releases the fluid at a constant rate to form the film.

The device has an additional advantage of being portable, and thus, it is capable of use at bedside in a hospital or clinic. The devices currently available for spreading monolayered blood films are too bulky for portable use. In fact, such devices seldom are removed from the laboratory. The procedure in most hospitals is to draw the blood sample from the patient, place the sample in a collection vial and take the sample to the laboratory for analysis. Use of the present device permits an immediate analysis of the blood by spreading a film at the time the blood is drawn.

This ability to spread the sample immediately after collection has several advantages. The intermediate step of placing the sample in a vial prior to analysis may be avoided. Collection vials may contain residual amounts of complexing agents or cleaning solutions which can contaminate the sample. For example, even small quantities of a complexing agent like disodium edetate (EDTA) can remove enough metal ions, including calcium and magnesium, from a red blood cell to distort the shape of the cell. Avoidance of this storage step prior to analysis of the sample prevents this possibility of contamination.

In addition, the volume of blood needed for a microscopic analysis is decreased. Rather than drawing a volume of blood sufficient to fill the collection vial, only a droplet of blood is required. Therefore, the sample can be obtained merely by pricking the finger with a sharp instrument, placing the droplet directly on the slide and spreading immediately the droplet collected. This feature makes the device of the present invention particularly useful in pediatrics since infants have little blood to spare for frequent blood tests using a conventional method of smearing films.

It will be understood, of course, that various changes and modifications may be made in the above described apparatus without departing from the spirit thereof, particularly as defined in the following claims.

What is claimed to be new and is desired to be secured by Letters Patent is:

1. A spreader for forming a monolayered film on a slide or the like from a fluid placed on the slide, said slide being held by a supporting surface, said spreader comprising:
    (a) a support having an upper surface and a lower surface;
    (b) a bar extending in a transverse direction and downwardly along said lower surface of said support, having a first sloped surface, a second sloped surface and a flat section interposed between the lower ends of said first and second sloped surfaces, said sloped surfaces extending upwardly toward the lower surface of said support from said flat section, said flat section and sloped surfaces extending in said transverse direction; and
    (c) means extending downwardly from said lower surface of said support along either side of said bar and slightly below said bar to engage said slide and to slightly space the flat section of said bar parallel to the slide or the like on which the monolayered film is to be formed.

2. A spreader as set forth in claim 1 wherein said support comprises a planar surface and said bar is secured to the lower surface thereof.

3. A spreader as set forth in claim 1 or 2 wherein said means extending downwardly from said lower surface of said support comprises pads mounted on either side of said bar and slightly below said bar to engage said slide and to slightly space the flat section of said bar parallel to the slide on which the monolayered film is to be formed.

4. A spreader as set forth in claim 3 further including means extending downwardly from said support having legs on either side of said support for engaging the supporting surface when the slide is engaged by the pads.

5. A spreader as set forth in claim 3 wherein said pads hold said support above the slide with said bar in close proximity to the slide whereby as the spreader is moved over the slide having a fluid thereon, a fluid sample contacts said flat section of said bar and the fluid sample is spread by capillary action across the slide to form a film.

6. A spreader as set forth in claim 1 including at least one handle on the upper surface of said support for gripping the spreader to maintain a constant pressure between the spreader and a slide as the spreader is moved over the slide.

7. A base for use with a spreader as claimed in claim 5 to form a monolayered film on a slide or the like comprising:
    (a) a supporting surface including a recess therein having parallel longitudinal sides for holding a slide in a stationary position;
    (b) means on the supporting surface for guiding the legs of the spreader and preventing lateral movement of the spreader as the spreader is moved over a slide held within the recess; and
    (c) ramp means at one end of said guiding means for receiving the legs of the spreader to lift the spreader from the supporting surface whereby said bar is evenly disengaged from contact with the film.

8. A base as set forth in claim 7 wherein said means on the supporting surface for guiding the legs of the spreader and preventing lateral movement of the spreader comprises two tracks on the supporting surface and adjacent the recess, said tracks being parallel to the parallel longitudinal sides of the recess and to each other.

9. A device for forming a monolayered film on a slide or the like from a fluid placed on the slide comprising a spreader and a base, said spreader including a support having an upper surface and a lower surface, a bar extending in a transverse direction and downwardly along said lower surface of said support, having a first sloped surface, a second sloped surface and a flat section interposed between the lower ends of said first and second sloped surfaces, said sloped surfaces extending upwardly toward the lower surface of said support from said flat section, said flat section and sloped surfaces extending in said transverse direction, and means extending downwardly from said lower surface of said support along either side of said bar and slightly below said bar to engage said slide and to slightly space the flat section of said bar parallel to the slide or the like on which the monolayered film is to be formed, and means extending downwardly from said lower surface of said support having legs on either side of said support for engaging the base, said base comprising a supporting surface including a recess therein having parallel longitudinal sides for holding a slide in a stationary position, means on the supporting surface for guiding the legs of the spreader and preventing lateral movement of the spreader as the spreader is moved over the slide held within the recess, and ramp means at one end of said guiding means for receiving the legs of said spreader to lift the spreader from the supporting surface whereby said bar is disengaged evenly from contact with the film.

10. A device as set forth in claim 9 wherein said support comprises a planar surface and said bar is secured to the lower surface thereof.

11. A device as set forth in claim 9 wherein said means extending downwardly from said lower surface of said support comprises pads mounted on either side of said bar and slightly below said bar to engage a slide and to slightly space the flat section of said bar from the slide on which the monolayered film is to be formed.

12. A device as set forth in claim 11 wherein said pads hold said support above said slide with said bar in close proximity to the slide whereby as the spreader is moved over the slide having a fluid thereon a fluid sample contacts said flat section of said bar and the fluid sample is spread by capillary action across the slide to form a monolayered film.

13. A device as set forth in claim 9 wherein the spreader includes at least one handle on the upper surface of said support for gripping the spreader to maintain a constant pressure between the spreader and the slide as the spreader is moved over the slide.

14. A device as set forth in claim 9 wherein said means on the supporting surface for guiding the legs of the spreader and preventing lateral movement of the spreader comprises two tracks on the supporting surface and adjacent the recess, said tracks being parallel to the parallel longitudinal sides of the recess and to each other.

* * * * *